(12) United States Patent
Nakayama (10) Patent No.: US 8,582,844 B2
(45) Date of Patent: Nov. 12, 2013

(54) MEDICAL IMAGE PROCESSING DEVICE AND METHOD

(75) Inventor: Naoko Nakayama, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 291 days.

(21) Appl. No.: 13/128,556

(22) PCT Filed: Nov. 10, 2009

(86) PCT No.: PCT/JP2009/069076
§ 371 (c)(1),
(2), (4) Date: May 10, 2011

(87) PCT Pub. No.: WO2010/055815
PCT Pub. Date: May 20, 2010

(65) Prior Publication Data
US 2011/0235878 A1    Sep. 29, 2011

(30) Foreign Application Priority Data
Nov. 13, 2008  (JP) .................................. 2008-290873

(51) Int. Cl.
*G06K 9/00*   (2006.01)

(52) U.S. Cl.
USPC ............ 382/128; 382/130; 382/131; 600/481

(58) Field of Classification Search
USPC .................... 382/128–131; 600/481
See application file for complete search history.

(56) References Cited

U.S. PATENT DOCUMENTS

| | | | |
|---|---|---|---|
| 5,125,410 A * | 6/1992 | Misono et al. ............... | 600/463 |
| 6,328,698 B1 * | 12/2001 | Matsumoto .................. | 600/481 |
| 7,920,734 B2 * | 4/2011 | Rinck et al. .................. | 382/131 |
| 8,068,894 B2 * | 11/2011 | Huizenga et al. ............ | 600/410 |
| 8,355,775 B2 * | 1/2013 | Oshiki et al. ................. | 600/425 |
| 2003/0236458 A1 * | 12/2003 | Hochman ..................... | 600/431 |
| 2004/0249270 A1 | 12/2004 | Kondo et al. | |
| 2006/0171585 A1 * | 8/2006 | Rinck et al. .................. | 382/173 |
| 2007/0244393 A1 * | 10/2007 | Oshiki et al. ................. | 600/463 |
| 2008/0118131 A1 | 5/2008 | Skinner et al. | |
| 2009/0054729 A1 * | 2/2009 | Mori et al. ................... | 600/114 |

FOREIGN PATENT DOCUMENTS

| | | |
|---|---|---|
| JP | 2004-283373 | 10/2004 |
| JP | 2006-75602 | 3/2006 |
| JP | 2006-167287 | 6/2006 |
| JP | 2007-275141 | 10/2007 |
| JP | 2007275141 A * | 10/2007 |
| JP | 2008-67991 | 3/2008 |
| JP | 2008-126070 | 6/2008 |
| WO | WO2005/117712 A1 | 12/2005 |
| WO | WO2007/129616 A1 | 11/2007 |

OTHER PUBLICATIONS

International Search Report in PCT/JP2009/069076.

* cited by examiner

*Primary Examiner* — Jayesh A Patel
*Assistant Examiner* — Iman K Kholdebarin
(74) *Attorney, Agent, or Firm* — Cooper & Dunham LLP (57) ABSTRACT

Extraction means configured to extract a blood vessel region from medical image data, detection means configured to perform evaluation regarding the shape or signal value distribution information in the periphery of a blood vessel including blood vessel contour points and the margin of blood vessel contour points in the blood vessel region extracted by the extraction means and detecting an abnormal portion on the basis of the evaluation result, and display means configured to display information regarding the abnormal portion detected by the detection means are provided.

13 Claims, 10 Drawing Sheets

MEDICAL IMAGE PROCESSING DEVICE AND METHOD

TECHNICAL FIELD

The present invention relates to a medical image processing device and method of performing analysis processing on a blood vessel.

BACKGROUND ART

As an image used for medical diagnosis in the related art, for example, a tomographic image of a subject photographed by an X-ray CT (Computed Tomography) apparatus, an MRI (Magnetic Resonance imaging) apparatus, or the like is known. In addition, a computer-aided detection apparatus (Computer-Aided Detection; hereinafter, referred to as CAD) has been developed which analyzes such a medical image using a computer, detects a lesion candidate from the shading, and presents it to a doctor. The CAD detects an image region (hereinafter, referred to as a lesion candidate region), which is presumed to be a lesion, automatically on the basis of the shape characteristic or density characteristic of the lesion in order to ease the burden on the doctor.

For example, Patent Document 1 or Patent Document 2 discloses a method of analyzing and displaying the constriction rate of a blood vessel. Specifically, in Patent Document 1, the constriction rate is calculated by assuming the shape of a temporary normal blood vessel on the basis of blood vessel shape information created from the image data and comparing the sizes of the sectional areas or diameters of the blood vessel and the temporary normal blood vessel with each other to detect a constricted portion.

In addition, in Patent Document 2, the constriction rate is calculated by correcting distortion of the blood vessel shape, assuming the shape of a temporary normal blood vessel on the basis of the blood vessel shape after correction, and detecting a constricted portion using the blood vessel and the temporary normal blood vessel.

PRIOR ART DOCUMENT

Patent Document

Patent Document 1: JP-A-2006-198708
Patent Document 2: JP-A-2005-162787

SUMMARY OF THE INVENTION

Problem to be Solved by the Invention

However, it has been pointed out that a coronary event (acute coronary syndrome), such as unstable angina or myocardial infarction, may occur due to destruction of atheroma plaque even when narrowing of a blood vessel lumen cannot be found. That is, in a series of processes (atheroma hardening process) in which atheroma plaque begins to be formed on a blood vessel wall and the blood vessel wall becomes thick toward the outside and is calcified gradually, lumen constriction in a blood vessel occurs at the final stage of the atheroma hardening process and does not appear as a constriction of a blood vessel before the stage.

The present invention has been made in view of the above problem, and it is an object of the present invention to provide a medical image processing device and method capable of performing evaluation even for the abnormalities in the periphery of the blood vessel which do not appear as a constriction.

Means of Solving the Problem

In order to achieve the above-described object, the present invention is a medical image processing device characterized in that it includes: extraction means configured to extract a blood vessel region from medical image data; detection means configured to perform evaluation regarding the shape or signal value distribution information for the periphery of a blood vessel including blood vessel contour points and the margin of blood vessel contour points in the blood vessel region extracted by the extraction means and detecting an abnormal portion on the basis of the evaluation result; and display means configured to display information regarding the abnormal portion detected by the detection means.

In addition, the evaluation regarding the shape or the signal value distribution information is performed on the basis of whether or not the shape of a first blood vessel region formed by blood vessel contour points and the margin of blood vessel contour points in the blood vessel region extracted by the extraction means and the shape of a second blood vessel region formed by blood vessel contour points of the blood vessel region are different from each other, and the detection means performs comparative evaluation regarding the shape or signal value distribution information for the first and second blood vessel regions and detects an abnormal portion on the basis of the evaluation result.

In addition, the extraction means extracts a first blood vessel region, which includes a high signal region with a higher signal value than a predetermined value, and a second blood vessel region, which does not include a high signal region, as the blood vessel region, and the detection means performs comparative evaluation regarding the shape or signal value distribution information for the first and second blood vessel regions and detects an abnormal portion on the basis of the evaluation result.

In addition, the detection means evaluates, for the blood vessel contour points, smoothness of distribution in a direction of a blood vessel core line and smoothness of distribution on a section perpendicular to the blood vessel core line and detects an abnormal portion in the periphery of the blood vessel on the basis of the evaluation result.

In addition, extended contour line setting means configured to set an extended contour line, which extends externally by a predetermined range from the blood vessel region extracted by the extraction means is further provided, and the detection means evaluates a signal value on the extended contour line set by the extended contour line setting means and detects an abnormal portion in the periphery of the blood vessel on the basis of the evaluation result.

In addition, reference creation means configured to set a plurality of normal sections, as reference sections, from the blood vessel region extracted by the extraction means and creating reference shapes and reference signal value distribution information of other sections on the basis of the plurality of set reference sections is further provided, and the detection means performs comparative evaluation of the reference shape and the reference signal value distribution information of each section, which are created by the reference creation means, and actual shape and signal value distribution information of the corresponding section and detects an abnormal portion on the basis of the evaluation result.

In addition, the detection means makes a further evaluation of a constriction of a blood vessel, and the display means displays an abnormal portion appearing as a constriction and an abnormal portion, which does not appear as a constriction, in different display forms.

Effect of the Invention

According to the present invention, it is possible to provide a medical image processing device and method capable of performing evaluation even for the abnormalities in the periphery of the blood vessel which do not appear as a constriction.

MODES FOR CARRYING OUT THE INVENTION

Hereinafter, preferred embodiments of the present invention will be described in detail with reference to the accompanying drawings.

First Embodiment

First, the configuration of an image processing system 1 to which a medical image processing device of the present invention is applied will be described.

Figure 1:
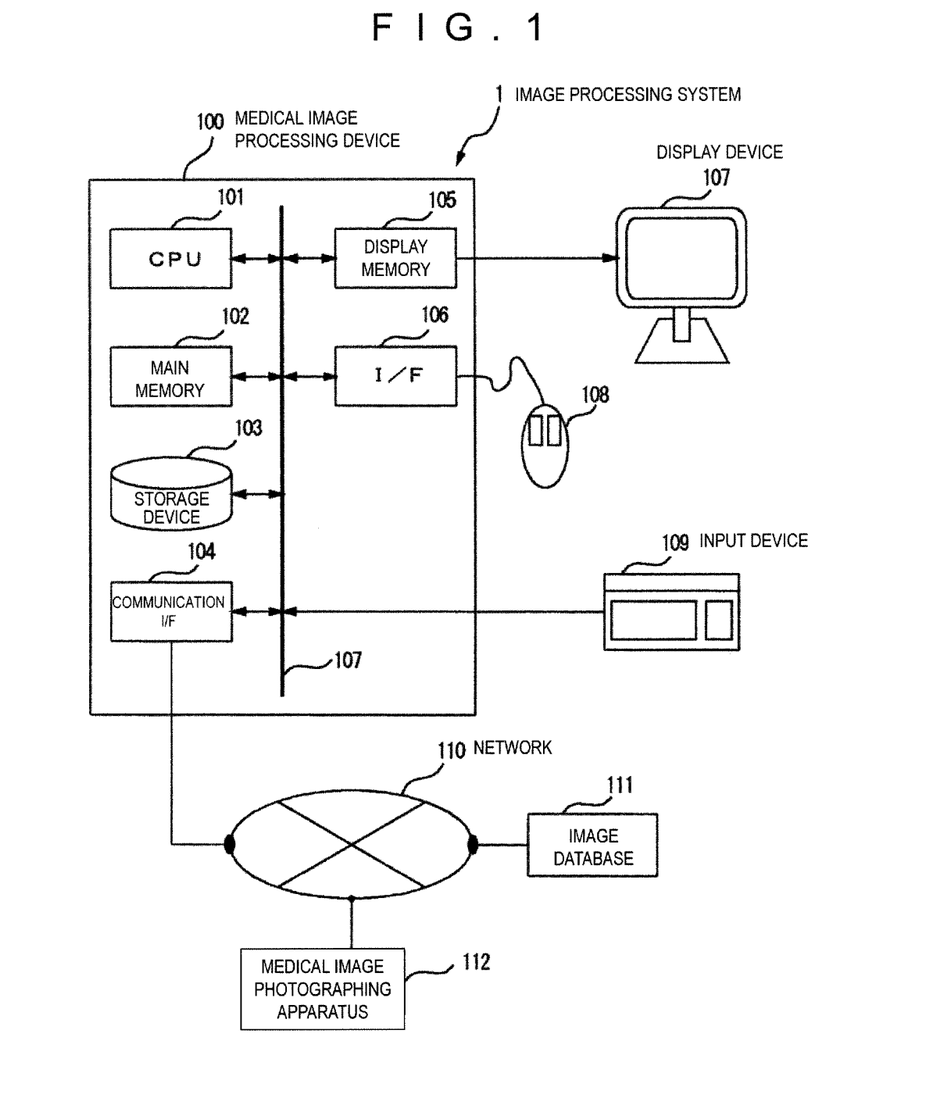
FIG. 1 is a hardware configuration view showing the entire configuration of an image processing system 1.

FIG. 1 is a hardware configuration view showing the entire configuration of the image processing system 1.

As shown in FIG. 1, the image processing system 1 includes: a medical image processing device 100 having a display device 107 and an input device 109; an image database 111 connected to the medical image processing device 100 through a network 110; and a medical image photographing apparatus 112.

The medical image processing device 100 is a computer for image diagnosis provided in a hospital or the like, and functions as a computer-aided detection apparatus (CAD) which analyzes a medical image, detects a lesion candidate from the shading, and presents it to a doctor.

The medical image processing device 100 includes a CPU (Central Processing Unit) 101, a main memory 102, a storage device 103, a communication interface (communication I/F) 104, a display memory 105, and an interface (I/F) 106 with an external device, such as a mouse 108, and these sections are connected to each other through a bus 107.

The CPU 101 loads a program stored in the main memory 102 or the storage device 103 to a work memory region on a RAM of the main memory 102 and executes it and performs driving control of each section connected through the bus 107 to realize various kinds of processing performed by the medical image processing device 100.

In addition, the CPU 101 extracts a blood vessel region on the basis of medical image data and executes processing, which will be described later, regarding detection of an abnormal portion in the periphery of the blood vessel (refer to FIGS. 2 and 5).

The main memory 102 is configured to include a ROM (Read Only Memory), a RAM (Random Access Memory), and the like. The ROM permanently holds a booting program of a computer, a program such as BIOS, data, and the like. In addition, the RAM temporarily holds a program, data, and the like loaded from the ROM, the storage device 103, and the like, and has a work area used when the CPU 101 performs various kinds of processing.

The storage device 103 is a storage device which performs reading/writing of data from/into an HDD (hard disk drive) or other recording media and a program executed by the CPU 101, data required when executing the program, an OS (operating system), and the like are stored therein. As programs, a control program equivalent to an OS and an application program are stored. Each of these program codes is read by CPU 101 when necessary and moved to the RAM of the main memory 102 and is executed as various kinds of means.

The communication I/F 104 has a communication control device, a communication port, and the like and mediates communication between the medical image processing device 100 and the network 110. In addition, the communication I/F 104 performs communication control with the image database 111, other computers, or the medical image photographing apparatus 112, such as an X-ray CT apparatus or an MRI apparatus, through the network 110.

The I/F 106 is a port for connection of a peripheral device and performs transmission and reception of data to and from the peripheral device. For example, an input device, such as the mouse 108, may be connected through the I/F 106.

The display memory 105 is a buffer which temporarily accumulates the display data input from the CPU 101. The accumulated display data is output to the display device 107 at a predetermined timing.

The display device 107 is formed by a liquid crystal panel, a display device such as a CRT monitor, and a logic circuit which cooperates with the display device to execute display processing and is connected to the CPU 101 through the display memory 105. The display device 107 displays the display data, which is accumulated in the display memory 105, on the display device by control of the CPU 101.

The input device 109 is an input device, such as a keyboard, for example, and outputs to the CPU 101 various kinds of instructions or information input by the operator. The operator operates the medical image processing device 100 interactively using the display device 107, the input device 109, and an external device such as the mouse 108.

The network 110 includes various communication networks, such as a LAN (Local Area Network), a WAN (Wide Area Network), an intranet, and the Internet, and mediates communication connection between the image database 111, a server, or other information devices and the medical image processing device 100.

The image database 111 accumulates and stores a medical image photographed by the medical image photographing apparatus 112 and is provided, for example, in a server of a hospital, a medical center, or the like. Although the image processing system 1 shown in FIG. 1 has a configuration in which the image database 111 is connected to the medical image processing device 100 through the network 110, the image database 111 may be provided, for example, in the storage device 103 of the medical image processing device 100.

In addition, although a medical image treated in the image processing system 1 of the present embodiment is tomographic images at a plurality of slice positions in the body axis direction which is photographed by an X-ray CT apparatus, a 3D image (three-dimensional volume image) obtained by overlapping of these tomographic images, or the like, the medical image is not limited thereto and may be set as a tomographic image or a 3D image photographed by an MRI apparatus or the like. Moreover, in the following explanation, an image in which a blood vessel region is displayed in a three-dimensional manner is called a 3D blood vessel image 38, a transverse section image perpendicular to the blood vessel core line is called a blood vessel transverse section image 35, and a longitudinal section image along the blood vessel core line is called a blood vessel longitudinal section image 31 (refer to FIG. 3).

Next, an operation of the image processing system 100 will be described with reference to FIGS. 2 to 8.

Figure 2:
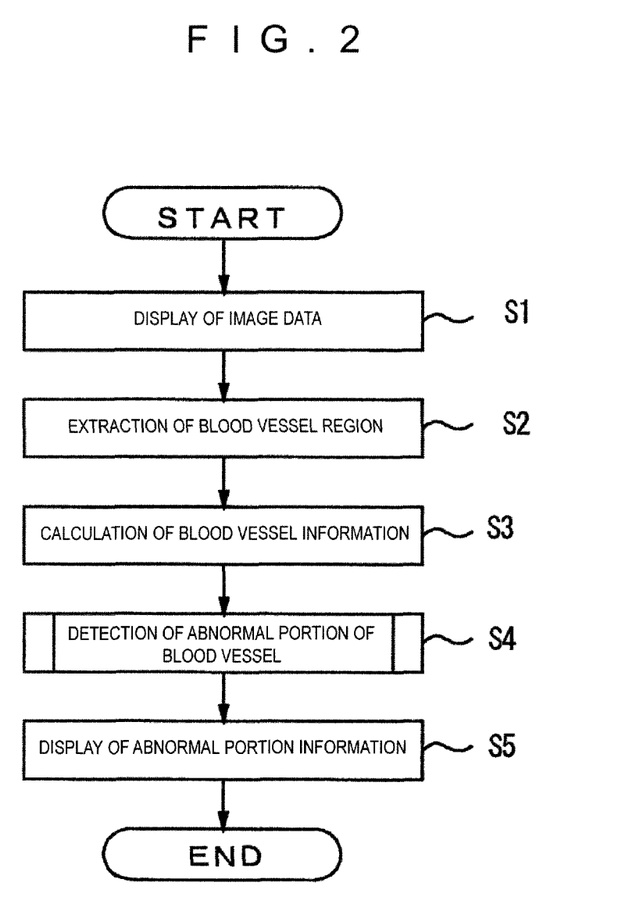
FIG. 2 is a flow chart showing the flow of entire image processing executed by a medical image processing device 100.

FIG. 2 is a flow chart showing the flow of entire image processing executed by the medical image processing device 100.

Figure 3:
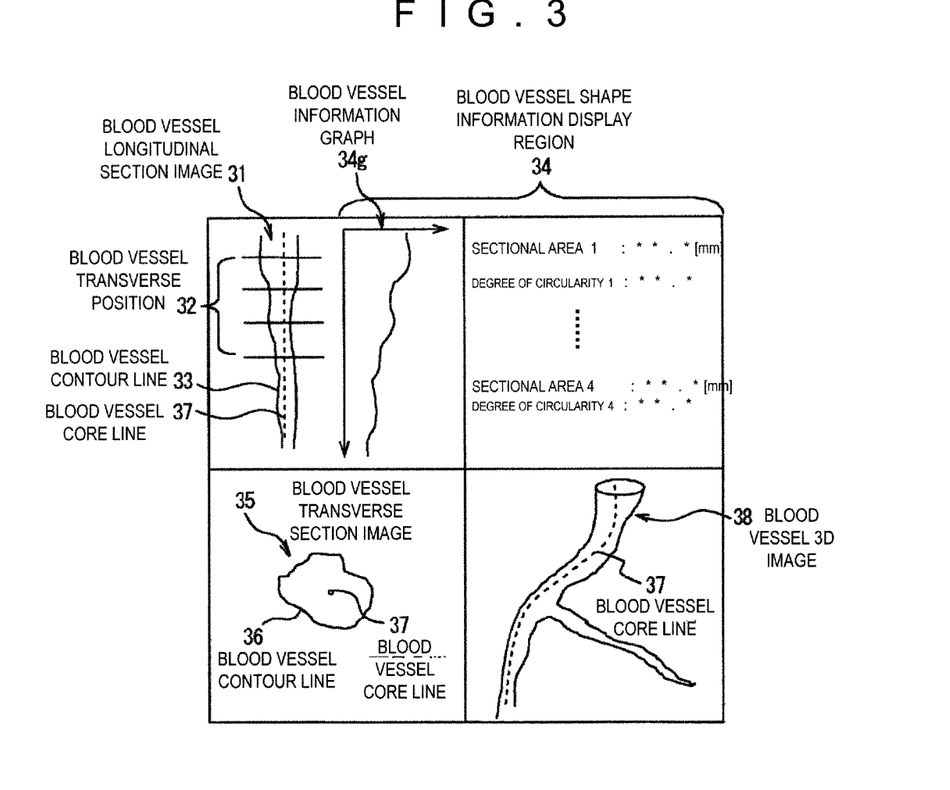
FIG. 3 is a view showing an example of a display screen when abnormal blood vessel portion detection processing is executed.

FIG. 3 is a view showing an example of a display screen when abnormal blood vessel portion detection processing is executed.

Figure 4:
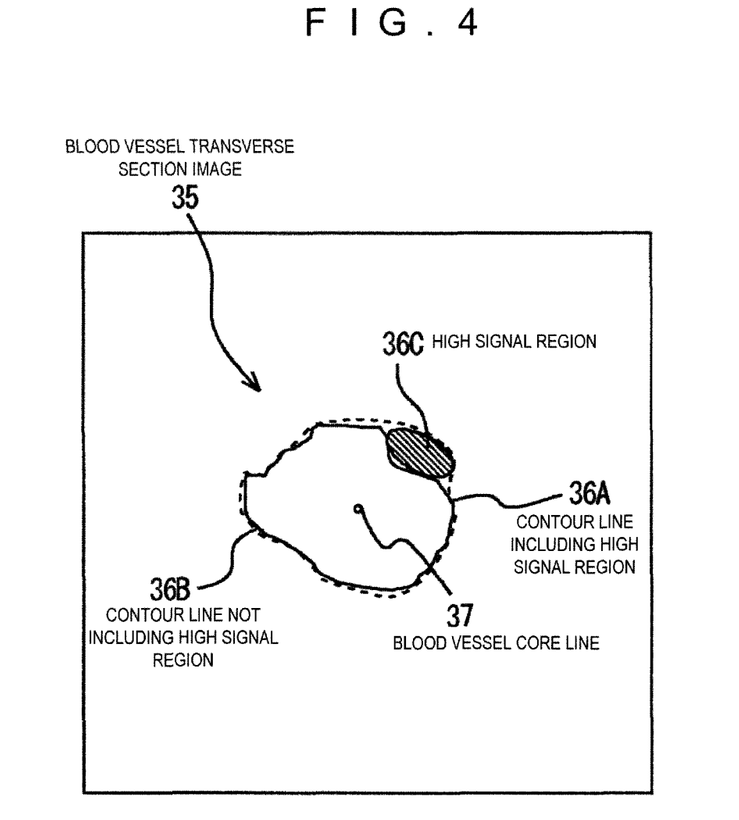
FIG. 4 is a view illustrating the extraction of a blood vessel region.

FIG. 4 is a view illustrating the extraction of a blood vessel region.

Figure 5:
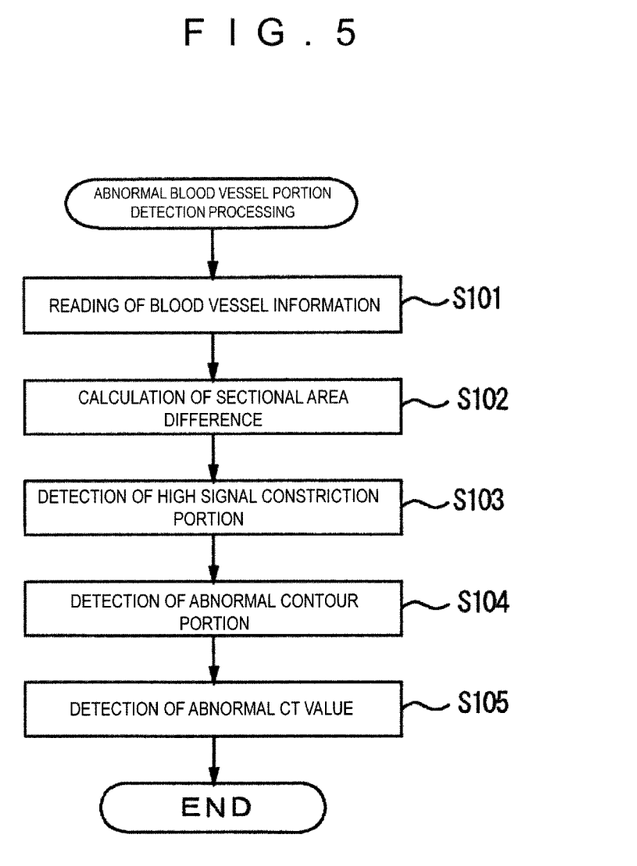
FIG. 5 is a flow chart illustrating the flow of processing regarding abnormal blood vessel portion detection executed by the medical image processing device 100.

FIG. 5 is a flow chart illustrating the flow of processing regarding the abnormal blood vessel portion detection executed by the medical image processing device 100.

Figure 6:
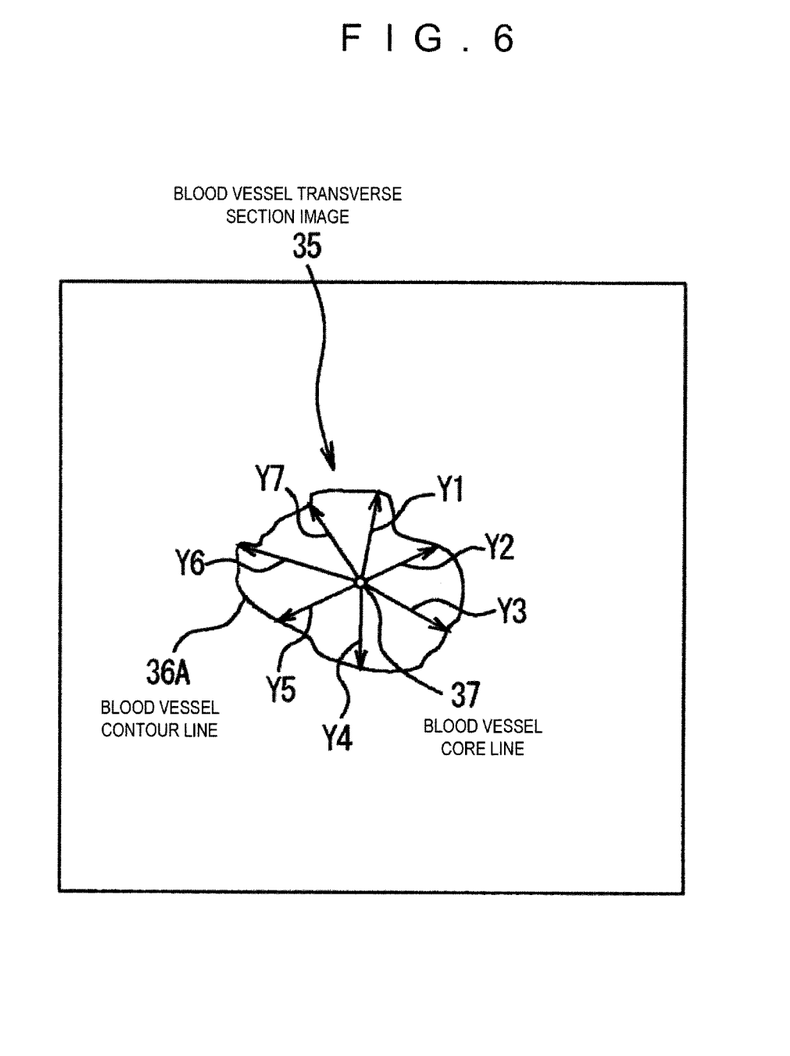
FIG. 6 is a view illustrating the evaluation of smoothness of blood vessel contour points on the blood vessel transverse section (direction perpendicular to the blood vessel core line).

FIG. 6 is a view illustrating the evaluation of smoothness of blood vessel contour points in the blood vessel transverse section image 35.

Figure 7:
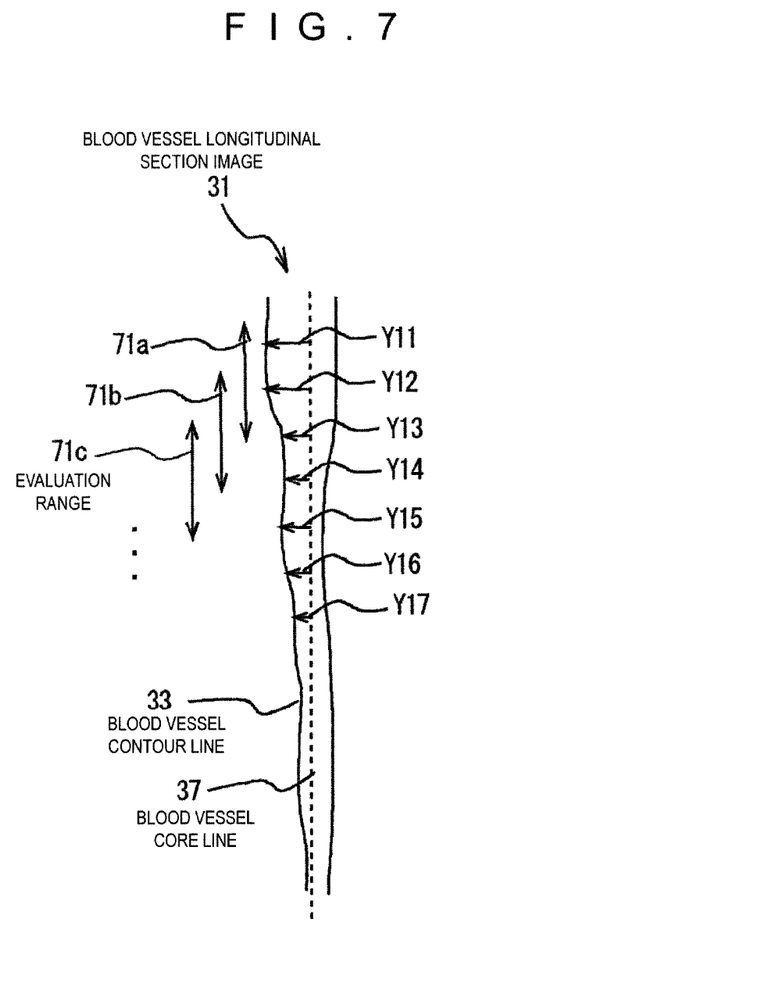
FIG. 7 is a view illustrating the evaluation of smoothness of blood vessel contour points on the blood vessel longitudinal section (direction of the blood vessel core line).

FIG. 7 is a view illustrating the evaluation of smoothness of blood vessel contour points in the blood vessel longitudinal section image 31.

Figure 8:
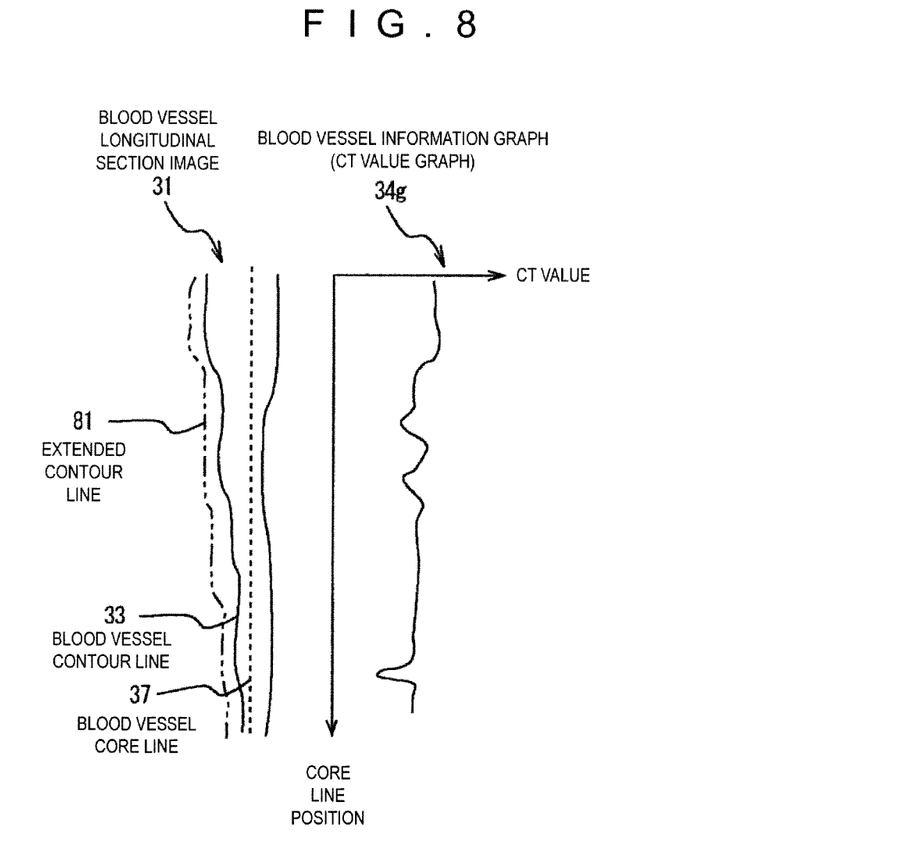
FIG. 8 is a view illustrating an extended contour line set near a blood vessel region.

FIG. 8 is a view illustrating an extended contour line set near the blood vessel region.

The CPU 101 of the medical image processing device 100 reads from the main memory 102 a program and data regarding image processing or abnormal blood vessel portion detection processing and executes the image processing and the abnormal blood vessel portion detection processing on the basis of the program and data.

In addition, it is assumed that the image data is acquired from the image database 111 or the like through the network 110 and the communication I/F 104 and stored in the storage device 103 of the medical image processing device 100 at the start of execution of the following image processing.

In the image processing of FIG. 2, the CPU 101 of the medical image processing device 100 performs processing of reading and displaying the image data first. The CPU 101 reads the selected image data from the storage device 103 and displays it on the display device 107 according to an instruction input through the operation of the input device 109, the mouse 108, or the like (step S101).

In the present embodiment, it is assumed that the image data including a blood vessel region is selected. In addition, the image displayed in this stage is assumed to be a 3D blood vessel image 38 obtained by overlapping of a plurality of tomographic images (refer to FIG. 3).

Then, when a desired blood vessel is designated from the operator through a mouse operation or the like on the displayed 3D blood vessel image 38, the CPU 101 extracts a region including a blood vessel core line of the blood vessel or a plurality of blood vessel contour points on sections perpendicular to the blood vessel core line as a blood vessel region.

Here, the blood vessel core line is a centerline of a blood vessel and is extracted by a vessel tracking method, for example. Specifically, when an operator designates a starting point, an end point, and a pass point in the blood vessel displayed on the display screen through a mouse operation or the like, the CPU 101 tracks the inside of the blood vessel between the designated points and extracts a blood vessel core line. In addition, the CPU 101 extracts a plurality of blood vessel contour points on each section which is perpendicular to the extracted blood vessel core line.

At the stage where the blood vessel core line or blood vessel contour points are extracted, the CPU 101 displays the extracted blood vessel core line on the 3D blood vessel image as shown in FIG. 3. In addition, the blood vessel longitudinal section image 31 along the blood vessel core line and the blood vessel transverse section image 35 are displayed on the display device 107.

Here, the extraction of a blood vessel contour point will be described with reference to FIG. 4. In the first embodiment, when extracting a blood vessel contour point, the CPU 101 extracts a contour line 36A (first blood vessel region) including a high signal region 36C with a higher signal value than a predetermined signal value and a contour line 36B (second blood vessel region) which does not include the high signal region 36C.

In FIG. 4, a shaded range is the high signal region 36C, a dotted line is the contour line 36A including the high signal region 36C, and a solid line is the contour line 36B which does not include the high signal region 36C.

Since a contrast medium is injected when photographing a blood vessel with an X-ray CT apparatus, a high signal value appears for the inside of the blood vessel compared with a region outside the blood vessel where the contrast medium is not injected. Moreover, in a portion calcified by hardening of plaque, a higher signal value than in a region where the contrast medium is injected appears.

Specifically, although the above-described CT values change with a state (amount or photographing timing) of contrast or the like, for example, the CT value of a calcified high signal region is set to about 350 to 1000, the CT value of a contrast region is set to about 130 to 350, and the CT value of a blood vessel wall (non-contrast region) is set to about 50 to 130.

The blood vessel contour point is a point as a boundary between a contrast region or the high signal region 36C and a blood vessel wall (non-contrast region), and the blood vessel contour line 36 is a line connecting blood vessel contour points on the same section.

The CPU 101 refers to the CT value distribution information on a plurality of lines, which extends in each direction on the section from a blood vessel core line 37, for the certain blood vessel transverse section image 35. In addition, a point having a larger CT value than a predetermined CT value α is assumed to be the high signal region 36C, and a region having a CT value which is equal to or smaller than the predetermined CT value α and is larger than a CT value β of a blood vessel wall is assumed to be a contrast region. The CPU 101 extracts a region including a contrast region and the high signal region 36C as a "first region (contour line 36A)" and extracts a region, which is a contrast region but does not include the high signal region 36C as a "second region (contour line 36B)". In addition, as the CT value α used as a threshold value of the high signal region 36C or the CT value β of a blood vessel wall, it is possible to use any of the values set in advance, the value calculated by the CPU 101, and the value input by the operator through the input device 109 or the like.

The CPU 101 may display the two extracted contour lines 36A and 36B on the blood vessel transverse section image 35, which is displayed on the display device 107, so as to overlap each other.

Then, the CPU 101 calculates the blood vessel information, such as the sectional area or diameter of each of the contour lines 36A and 36B, a degree of circularity, and a CT value on the basis of the extracted blood vessel region (the blood vessel core line 37 and the blood vessel contour line 36) and holds it in the main memory 102 (step S3).

At this stage, the CPU 101 may display the calculated blood vessel information in a blood vessel information display region 34, as shown in FIG. 3. In addition, as a display form of the blood vessel information, not only numerical display but also display, such as a blood vessel information graph 34g obtained by expressing the numeric value on the graph, is possible. In addition, color mapping display of the blood vessel longitudinal section image 31, the blood vessel transverse section image 35, the 3D blood vessel image 38, and the like may be performed according to each value of the blood vessel information.

Then, CPU 101 evaluates the presence of constriction of a blood vessel or the constriction rate, the shape in the periphery of the blood vessel, and the CT value distribution information on the basis of the calculated blood vessel information and detects an abnormal portion on the basis of the evaluation result (step S4; will be described later). The CPU 101 displays the information regarding the detected abnormal portion on the display device 107 (step S5). In display processing of abnormal portion information in step S5, the CPU 101 displays a constricted portion or the CT value calculated in step S4 using a numeric value or a graph or performs color mapping display corresponding to the numeric value. In addition, the CPU 101 is assumed to highlight the position of the detected abnormal portion with color display or graphic tools, such as an arrow. In addition, the CPU 101 displays an abnormal portion, which appears as a constriction, and an abnormal portion, which does not appear as a constriction but in which abnormalities in the shape or CT value distribution information appear, in different display forms.

Next, the abnormal blood vessel portion detection processing in step S4 of FIG. 2 will be described in detail with reference to FIG. 5.

In the first embodiment, in the blood vessel region extraction step (step S2) of FIG. 2, a blood vessel core line is first extracted and a region (contour line 36A) including a high signal region and a region (contour line 36B) not including a high signal region which are shown in FIG. 4 are extracted on the basis of the extracted core line.

As shown in the flow chart of FIG. 5, the CPU 101 reads the blood vessel information calculated in step S3 of FIG. 2 (step S101). In addition, the shapes of the two contour lines 36A and 36B extracted in step S2 of FIG. 2 are compared (step S102), thereby detecting a lumen constriction portion (high signal constriction portion) of a blood vessel (step S103). Here, the lumen constriction portion is equivalent to the high signal region 36C. As comparison of the shapes of the two contour lines 36A and 36B, for example, it is preferable to calculate a sectional area difference between the regions (contour lines 36A and 36B) and to detect the corresponding portion as a lumen constriction portion (abnormal portion) when the difference is equal to or larger than a predetermined value. In addition, instead of the sectional area difference, other feature amounts regarding the shape may be compared.

Then, the CPU 101 executes processing for detecting the abnormalities of a blood vessel contour shape for other portions, in which a lumen constriction portion is not detected, for the contour line 36A including a high signal region (step S104). Specifically, the CPU 101 evaluates the smoothness of the contour line 36A in the blood vessel transverse section image 35 perpendicular to the blood vessel core line 37 and the smoothness of the contour line 33 in the blood vessel longitudinal section image 31 along the blood vessel core line 37.

The smoothness of the contour line 36A in the blood vessel transverse section image 35 is assumed to be evaluated by calculating distances from the blood vessel core line 37 to a plurality of contour points on the contour line 36A like arrows Y1, Y2, Y3, Y4, Y5, Y6, and Y7 shown in FIG. 6 and using a variation in the calculated distances or the degree of circularity of the contour line 36A. The CPU 101 detects a sectional position, at which the value of distance variation or the degree of circularity indicates a value equal to or larger than a predetermined threshold value, as an abnormal contour portion. For example, variance, standard deviation, or the like may be preferably used as the distance variation.

The smoothness of the contour line 36A in the blood vessel traverse section 35 is assumed to be evaluated for each sectional position 32 (refer to FIG. 3).

For the smoothness of the contour line 33 in the blood vessel longitudinal section image 31, a distance from each point on the blood vessel core line 37 to the blood vessel contour line 33 is calculated as indicated by horizontal arrows Y11, Y12, Y13, Y14, Y15, Y16, and Y17 in FIG. 7. Since a blood vessel narrows toward the end, a plurality of evaluation ranges 71a, 71b, 71c, . . . are set in the core line direction and a distance variation is evaluated within each evaluation range. The CPU 101 detects an evaluation range, in which the value of distance variation indicates a value equal to or larger than a predetermined threshold value, as an abnormal contour portion. Similar to the blood vessel transverse section image 35, for example, variance, standard deviation, or the like may be preferably used as the distance variation.

The smoothness of the contour line 33 in the core line direction is assumed to be evaluated for the plurality of blood vessel longitudinal section images 31 rotation-displayed with the core line as an axis.

In addition, the CPU 101 detects the abnormalities of CT values in the periphery of the blood vessel in a predetermined distance range from the contour line 33 (step S105). That is, the CPU 101 sets an extended contour line 81 (that is, the periphery of a blood vessel) near the blood vessel contour line 33 as shown in FIG. 8.

In addition, the CPU 101 calculates the average of CT values of points on the extended contour line 81, calculates a difference between the calculated average CT value and a CT value at each contour point on the extended contour line 81, and detects a point, at which the calculated distance is equal to or larger than a predetermined threshold value, as an abnormal portion of CT value.

Here, it is preferable that a distance range corresponding to the target blood vessel is set as the range (position of an extended contour line) in the periphery of the blood vessel. In a major coronary portion, it is known that plaque (atheroma plaque) which has not hardened appears in a range extended externally by about 0.5 mm from a blood vessel with a thickness of about 3 to 4 mm. Therefore, for example, in a blood vessel of about 3 to 4 mm which is close to the origin, it is preferable that the extended contour line 81 is provided externally by about 0.5 mm or about 5 pixels from the contour line 33. In addition, the range of in the periphery of the blood vessel may be determined by the rate using the thickness of a blood vessel instead of a distance. In addition, as the range in the periphery of the blood vessel, it is possible to use any of the values set in advance, the value calculated by the CPU 101, and the value input by the operator through the input device 109 or the like.

It is known that in the early stage of an atheroma hardening process, a blood vessel structure changes in the form of thickening of a blood vessel wall. Through processing in step S104 or step S105, plaque which has not hardened can be detected from an image of a blood vessel region (54-th Annual Meeting of Japanese College of Cardiology, Fireside Symposium 5: Clinical Frontiers using 64-row multi-slice CT "Cardiovascular diagnosis by multi-slice CT", pp. 15-20).

As described above, in the image processing system 1 of the first embodiment, the CPU 101 of the medical image processing device 100 extracts a region (contour line 36A) including the high signal region 36C with a higher CT value than a predetermined value and a region (contour line 36B) not including the high signal region 36C on the basis of the read medical image data, compares the shapes (for example, sectional areas) of the extracted contour lines 36A and 36B, and detects calcified plaque (lumen constriction portion). In addition, the smoothness of distribution in a direction of blood vessel core line and the smoothness of distribution on a section perpendicular to the blood vessel core line are evaluated for blood vessel contour points, and a portion with a predetermined variation is detected as an abnormal portion.

In addition, the CPU 101 sets the extended contour line 81, which is obtained by extending blood vessel contour points externally by a predetermined range, and detects an abnormal portion, such as plaque which has not hardened, appearing in the periphery of the blood vessel by evaluating the CT value on the set extended contour line 81. Then, the CPU 101 displays the detected abnormal portion on the blood vessel image.

Accordingly, when diagnosing an abnormal portion of a blood vessel, not only lumen constriction of the blood vessel can be detected, but also plaque or the like which has not been yet calcified and appears in the periphery of the blood vessel can be detected. As a result, since a comprehensive evaluation of a blood vessel including the abnormalities in a relatively early stage in the atheroma hardening process becomes possible, the precision of blood vessel analysis is improved.

In addition, in the above explanation, the CT value is denoted as a signal value because an abnormal portion or the like is detected from a CT image. However, in the case where an MRI image or the like is used, a brightness value is used as a signal value.

In addition, the CT value or the specific numeric value of the distance (or the pixel value) set as an extended contour line is an example. When blood vessels to be evaluated are different, it is preferable to set an appropriate value for each blood vessel.

Moreover, in the present embodiment, a region including a high signal region as a blood vessel region, which has a signal value higher than a predetermined value, is set as the first blood vessel region and a region not including a high signal region as a blood vessel region is set as the second blood vessel region. However, a region formed by blood vessel contour points and the margin of blood vessel contour points in a blood vessel region may be set as the first blood vessel region and a region formed by blood vessel contour points of the blood vessel region may be set as the second blood vessel region. That is, the evaluation regarding the shape or the signal value distribution information may be performed on the basis of whether or not the shape of the first blood vessel region formed by blood vessel contour points and the margin of blood vessel contour points in the blood vessel region extracted by the extraction means and the shape of the second blood vessel region formed by blood vessel contour points of the blood vessel region are different from each other.

Second Embodiment

Next, the image processing system 1 of a second embodiment will be described. Since the hardware configuration of the image processing system 1 of the second embodiment is the same as that of the image processing system 1 of the first embodiment in FIG. 1, explanation thereof will be omitted, and the same reference numerals are given to the same sections for explanation.

Figure 9:
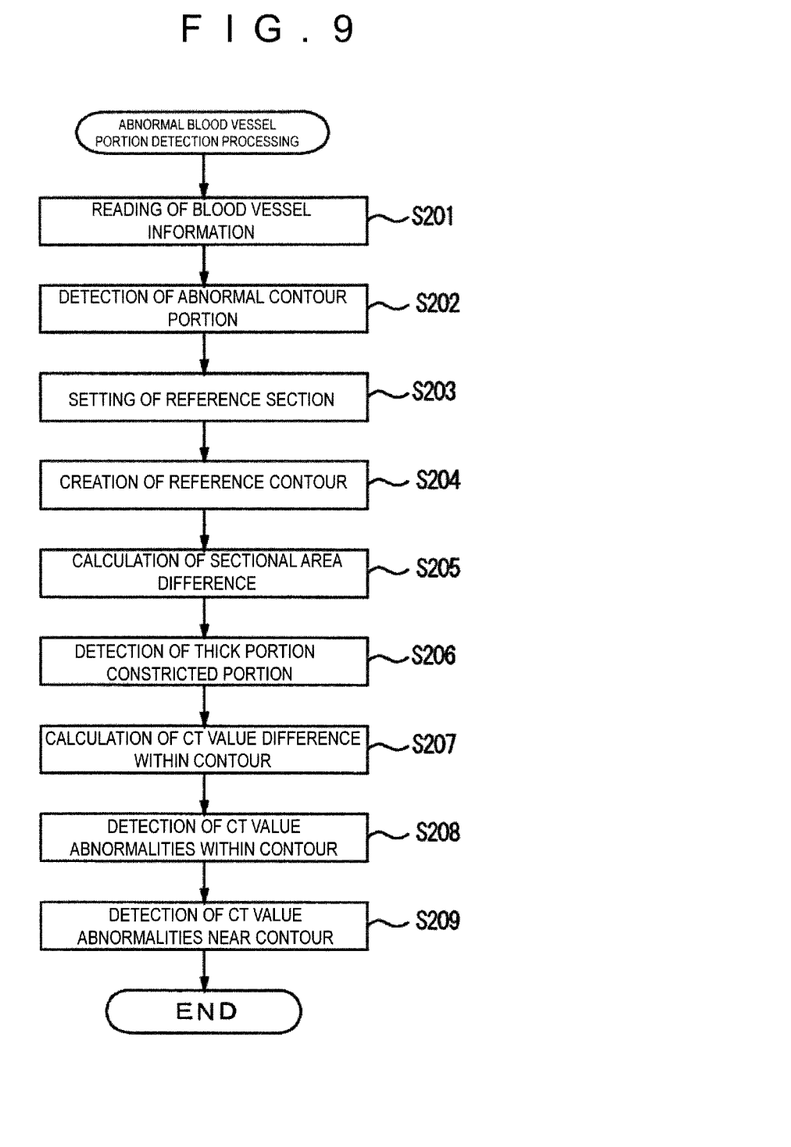
FIG. 9 is a flow chart showing the flow of abnormal blood vessel portion detection processing in a second embodiment.
Figure 10:
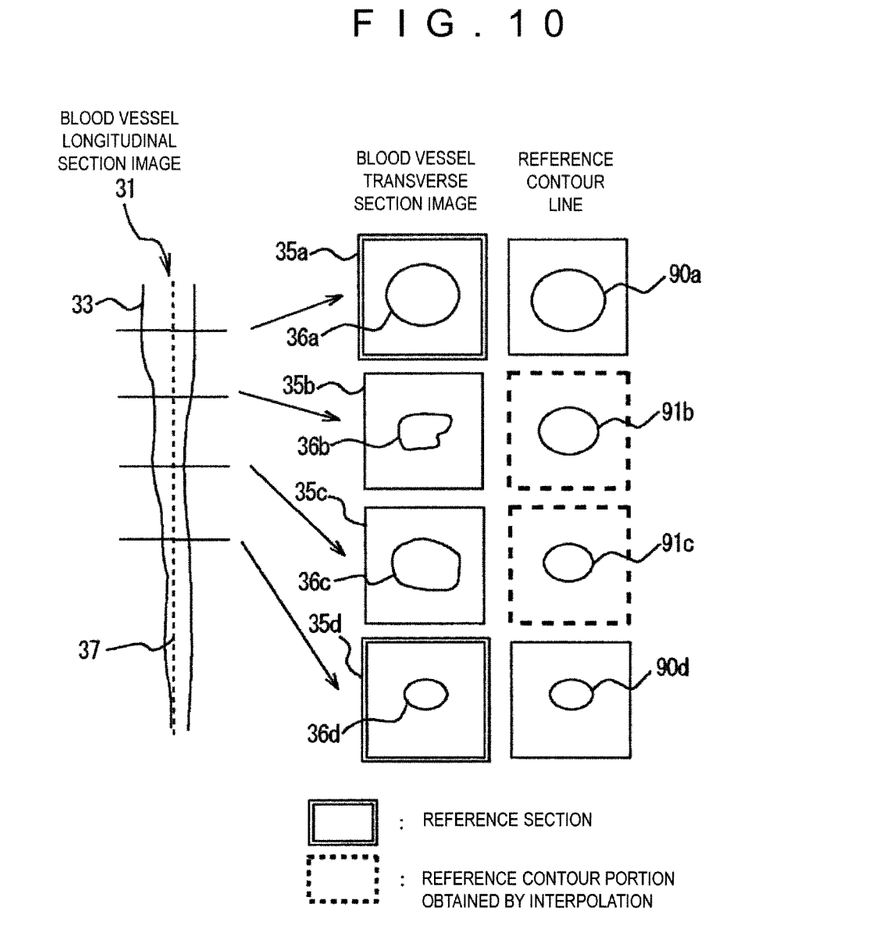
FIG. 10 is a view illustrating a reference contour line.

FIG. 9 is a flowchart showing the flow of abnormal blood vessel portion detection processing in the second embodiment, and FIG. 10 is a view illustrating a reference contour line.

In the second embodiment, abnormal blood vessel portion detection processing shown in the flow chart of FIG. 9 is performed in the abnormal portion detection step (step S4) of the image processing shown in FIG. 2.

As shown in FIG. 9, the CPU 101 reads the blood vessel information calculated in step S3 of FIG. 2 (step S201), and detects an abnormal portion of the contour line first (step S202). For detection of an abnormal portion of the contour line, it is preferable to perform the same processing as step S102 (calculation of a sectional area difference between a region including a high signal region and a region not including a high signal region) or step S104 (evaluation of the smoothness of a contour line) in the first embodiment (FIG. 5). The CPU 101 detects at least two sections, which have no abnormalities in the shape of a contour line and in which a standard deviation of CT values within the contour indicates a predetermined value or less, before and after the detected abnormal portion of the contour line and sets these as reference sections (step S203).

In the following explanation, an example of setting the reference section for the blood vessel transverse section image 35 will be described. In addition, an operator may set the reference section by operating the mouse 108 or the input device 109 while referring to a displayed blood vessel image.

In the example shown in FIG. 10, among blood vessel transverse section images 35*a*, 35*b*, 35*c*, and 35*d*, the transverse section images 35*a* and 35*d* are presumed to be normal. The CPU 101 extracts a blood vessel contour line from each of the transverse section images 35*a* and 35*d* presumed to be normal and sets the extracted blood vessel contour lines as reference contour lines 90*a* and 90*d*.

The CPU 101 creates reference contour lines 91*b* and 91*c* at transverse section positions on the basis of the reference contour lines 90*a* and 90*d* using linear interpolation (step S204). Moreover, for the transverse section images 35*a*, 35*b*, 35*c*, and 35*d*, for example, feature amounts indicating the shapes, such as sectional areas, are compared between the actual contour lines 36*a*, 36*b*, 36*c*, and 36*d* extracted in step S2 of FIG. 2 and the reference contour lines 90*a*, 91*b*, 91*c*, and 90*d* set or created in steps S203 and S204 of FIG. 9, and a thick portion·constricted portion is detected (step S206). Here, each of the contour lines 36*a*, 36*b*, 36*c*, and 36*d* may be either the contour line including a high signal region or the contour line not including a high signal region.

In addition, the CPU 101 calculates a difference between standard deviations of CT values within contour lines for a contour line on the reference section and an adjacent contour line among contour lines on other sections (step S207) and detects the corresponding portion as an abnormal CT value portion within the contour when the difference is a predetermined threshold value and above (step S208). Specifically, as shown in FIG. 10, the CPU 101 calculates a difference between the standard deviation of CT values within the actual contour line 36a of the reference section 35a and the standard deviation of CT values within the contour line 36b on the adjacent section 35b and detects the corresponding portion as an abnormal CT value portion within the contour when the difference is equal to or larger than a predetermined threshold value. Although the standard deviation is mentioned as an example for expressing the difference of CT values herein, a difference of average CT values, a difference of maximum CT values, or a difference of minimum CT values within contour lines may be used.

In addition, the CPU 101 detects the abnormalities of CT values in the periphery of the blood vessel in a predetermined distance range from the contour line (step S209). In step S209, in the same manner as in step S105 of FIG. 5, the CPU 101 sets the extended contour line 81 near the blood vessel contour line 33, calculates the average of CT values of points on the extended contour line 81, calculates a CT value difference between the calculated average CT value and each contour point on the extended contour line 81, and detects as an abnormal CT value portion a point at which the calculated difference is equal to or larger than a predetermined threshold value.

In the example of FIG. 10, although the contour line 36c of the transverse section image 35c shows a shape which is not detected as an abnormal portion in the abnormal portion detection processing of the first embodiment or the abnormal contour portion detection processing of step S202 in FIG. 9, it is thick as a whole compared with the previous and next sections 35b and 35d. If the reference contour line 91c is created and the created reference contour line 91c is compared with the actual contour line 36c similar to the second embodiment, the abnormalities of the shape (sectional area or the like) are detected.

As described above, in the second embodiment, the CPU 101 of the medical image processing device 100 sets sectional images, which are presumed to be normal from the blood vessel section images 35a, 35b, 35c, and 35d at the respective sectional positions, on the reference sections 35a and 35d and extracts blood vessel contour lines on the reference sections and sets them as the reference contour lines 90a and 90d. Moreover, for one blood vessel, the CPU 101 creates the reference contour lines 91b and 91c on the other sections from the blood vessel contour lines 90a and 90d on at least two reference sections. In addition, the CPU 101 compares the shapes of the contour lines 36a, 36b, 36c, and 36d, which are actually extracted from the sectional images 35a, 35b, 35c, and 35d, with the corresponding reference contour lines 90a, 91b, 91c, and 90d and detects the corresponding portion as a constricted portion when the difference is large.

In addition, the CPU 101 compares the CT value distribution information within the contour line 36a (or 36d) on the reference section 35a (or 35d) with the CT value distribution information within the contour line 36b (or 36c) at the adjacent sectional position and detects a section, which has a large difference of CT value distribution information, as a CT value abnormal portion within the contour. In addition, the CPU 101 sets an extended contour line, which extends externally by a predetermined range from the extracted contour line 33 and detects an abnormal portion related to the CT value of each point on the extended contour line as an abnormal CT value portion in the periphery portion.

Therefore, in addition to the effects obtained in the medical image processing device 100 of the first embodiment, a portion in which the shape or the CT value distribution is not detected as abnormalities because the entire blood vessel is thick can be accurately detected as an abnormal portion. In addition, since the reference contour line can be set or created from the target blood vessel image, it becomes possible to evaluate each blood vessel more accurately.

In addition, although an example where the reference section is a transverse section is shown in the above explanation, a longitudinal section may also be set as the reference section.

While the preferred embodiments of the image processing device related to the present invention have been described, the present invention is not limited to the above-described embodiments. For example, the methods described in the first and second embodiments may be appropriately combined. In addition, it is apparent to those skilled in the art that various changes and modifications can be made within the range of the technical idea disclosed in this specification, and it should undoubtedly be understood that they also belong to the technical range of the present invention.

DESCRIPTION OF REFERENCE NUMERALS

1: image processing system
100: medical image processing device
101: CPU
102: main memory
103: storage device
104: communication I/F
105: display memory
106: I/F
107: display device
108: mouse (external device)
109: input device
110: network
111: image database
31: blood vessel longitudinal section image
33: blood vessel contour line in blood vessel longitudinal section image
35: blood vessel transverse section image
37: blood vessel core line
36: blood vessel contour line in blood vessel transverse section image
36A: blood vessel contour line including high signal region
36B: blood vessel contour line not including high signal region
81: extended contour line
90a, 90d: reference contour line
91a, 91d: reference contour line created by interpolation

The invention claimed is:
1. A medical image processing device comprising:
extraction means configured to extract a blood vessel region from medical image data;
detection means configured to perform evaluation regarding the shape or signal value distribution information in the periphery of a blood vessel including blood vessel contour points and the margin of blood vessel contour points in the blood vessel region extracted by the extraction means and detecting an abnormal portion on the basis of the evaluation result;

display means configured to display information regarding the abnormal portion detected by the detection means; and extended contour line setting means configured to set an extended contour line, which extends externally by a predetermined distance in radius direction from the blood vessel region along a blood vessel core line, wherein the detection means evaluates a signal value on the extended contour line set by the extended contour line setting means and detects the abnormal portion in the periphery of the blood vessel on the basis of the evaluation result.

2. The medical image processing device according to claim 1, wherein the evaluation regarding the shape or the signal value distribution information is performed on the basis of whether or not the shape of a first blood vessel region formed by blood vessel contour points and the margin of blood vessel contour points in the blood vessel region extracted by the extraction means and the shape of a second blood vessel region formed by blood vessel contour points of the blood vessel region are different from each other, and the detection means performs comparative evaluation regarding the shape or signal value distribution information for the first and second blood vessel regions and detects an abnormal portion on the basis of the evaluation result.

3. The medical image processing device according to claim 1, wherein the extraction means extracts a first blood vessel region, which includes a high signal region with a higher signal value than a predetermined value, and a second blood vessel region, which does not include a high signal region, as the blood vessel region, and the detection means performs comparative evaluation regarding the shape or signal value distribution information for the first and second blood vessel regions and detects an abnormal portion on the basis of the evaluation result.

4. The medical image processing device according to claim 1, wherein the detection means evaluates, for the blood vessel contour points, smoothness of distribution in a direction of a blood vessel core line and smoothness of distribution on a section perpendicular to the blood vessel core line and detects an abnormal portion in the periphery of the blood vessel on the basis of the evaluation result.

5. The medical image processing device according to claim 1, further comprising:

reference creation means configured to set a plurality of normal sections, as reference sections, from the blood vessel region extracted by the extraction means and creating reference shapes and reference signal value distribution information of other sections on the basis of the plurality of set reference sections, wherein the detection means performs comparative evaluation of the reference shape and the reference signal value distribution information of each section, which are created by the reference creation means, and actual shape and signal value distribution information of the corresponding section and detects an abnormal portion on the basis of the evaluation result.

6. The medical image processing device according to claim 1, wherein the detection means evaluates constriction of a blood vessel further, and the display means displays an abnormal portion appearing as a constriction and an abnormal portion, which does not appear as a constriction, in different display forms.

7. A medical image processing method comprising:

an extraction step of extracting a blood vessel region from medical image data;

a detection step of performing evaluation regarding the shape or signal value distribution information in the periphery of a blood vessel including blood vessel contour points and the margin of blood vessel contour points in the blood vessel region extracted in the extraction step and detecting an abnormal portion on the basis of the evaluation result;

a display step of displaying information regarding the abnormal portion detected in the detection step; and a setting step of setting an extended contour line, which extends externally by a predetermined distance in radius direction from the blood vessel region along a blood vessel core line, wherein the detection step evaluates a signal value on the extended contour line set by the setting step and detects the abnormal portion in the periphery of the blood vessel on the basis of the evaluation result.

8. The medical image processing method according to claim 7, wherein the evaluation regarding the shape or the signal value distribution information is performed on the basis of whether or not the shape of a first blood vessel region formed by blood vessel contour points and the margin of blood vessel contour points in the blood vessel region extracted by the extraction step and the shape of a second blood vessel region formed by blood vessel contour points of the blood vessel region are different from each other, and in the detection step, comparative evaluation regarding the shape or signal value distribution information is performed for the first and second blood vessel regions and an abnormal portion is detected on the basis of the evaluation result.

9. The medical image processing method according to claim 7, wherein in the extraction step, a first blood vessel region including a high signal region with a higher signal value than a predetermined value and a second blood vessel region not including a high signal region are extracted as the blood vessel region, and in the detection step, comparative evaluation regarding the shape or signal value distribution information is performed for the first and second blood vessel regions and an abnormal portion is detected on the basis of the evaluation result.

10. The medical image processing method according to claim 7, wherein in the detection step, smoothness of distribution in a direction of a blood vessel core line and smoothness of distribution on a section perpendicular to the blood vessel core line are evaluated for the blood vessel contour points, and an abnormal portion in the periphery of the blood vessel is detected on the basis of the evaluation result.

11. The medical image processing method according to claim 7, further comprising:

a reference creation step of setting a plurality of normal sections, as reference sections, from the blood vessel region extracted in the extraction step and creating reference shapes and reference signal value distribution information of other sections on the basis of the plurality of set reference sections, wherein in the detection step, comparative evaluation of the reference shape and the reference signal value distribution information of each section, which are created in the reference creation step, and actual shape and signal value distribution information of the corresponding section is performed and an abnormal portion is detected on the basis of the evaluation result.

12. The medical image processing method according to claim 7, wherein in the detection step, constriction of a blood vessel is further evaluated, and in the display step, an abnormal portion appearing as a constriction and an abnormal portion, which does not appear as a constriction, are displayed in different display forms.

13. The medical image processing device according to claim 1, wherein the evaluation result is a difference between a signal value at each point on the extended contour line and an average value of the signal values of points on the extended contour line.

* * * * *